United States Patent [19]

Bailey

[11] Plant 4,857

[45] Jun. 15, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,443

[22] Filed: Sep. 9, 1980

[51] Int. Cl.[3] ..... A01H 5/00

[52] U.S. Cl. ..... Plt./22

[58] Field of Search ..... Plt./22

*Primary Examiner*—James R. Feyrer

*Attorney, Agent, or Firm*—Vincent G. Gioia

[57] ABSTRACT

A new floribunda rose variety of multi-lavender tone coloring.

1 Drawing Figure

1

The present invention relates to a new and distinct variety of rose plant of the floribunda rose class, which was originated by my crossing as seed parent the rose known as "Angel Face" and an unnamed, unreleased seedling of my creation as pollen parent.

Among the novel characteristics possessed by this new variety which distinguish it from its parents and all other varieties of which I am aware are a floriferous quality of producing many flowers of overall lavender tonality borne singly and in large sprays on a vigorous, free branching, spreading plant with abundant foliage and superior disease resistance. Asexual reproduction by budding of the new variety as performed in Kern County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "48A" is plate 48A of the Royal Horticultural Society Color Chart.

Parentage: Seedling.

*Seed parent.*—"Angel Face".

*Pollen parent.*—Unnamed unpatented, unreleased seedling of my creation.

Class: Floribunda.

The following observations are made of specimens grown outdoors in Kern County, Calif. during the month of November.

1. FLOWER

Blooming habit: Continuous.

A. Bud (1) *Size.*—Medium.

(2) *Form.*—Ovoid.

(3) *Color.*—After sepals fall petals appear patched in two tone near 48A and 51C to D.

(4) *Sepals.*—Simple, short, not longer than bud.

2

(5) *Peduncle.*—Length — short, 1 to 1½ inches. Aspect — straight, thin. Strength — erect, wire-like. Color — reddish green 137C.

B. Bloom:

(1) *Size.*—Average size when fully expanded — about 3½ inches.

(2) *Borne.*—Singly and in large sprays.

(3) *Form.*—Loosely recurved with ruffled effect.

(4) *Petalage.*—Number of petals under normal conditions — about 28 to 32.

(5) *Color.*—Petal coloring both top and underside surfaces generally retains bud colors 48A and 51C to D. Inner petals of freshly opened flowers are more lightly colored than outer petals. As flowers open further and mature, general tonality remains the same but highlights of 56A appear and color of older blooms may darken inner and outer petals uniformly with age. General appearance takes on a more uniform overall lavender to rose tonality.

C. Petals:

(1) *Texture.*—Medium thick.

(2) *Appearance.*—Soft velvety.

(3) *Form.*—Rounded.

(4) *Arrangement.*—Imbricated and ruffled when flower opens.

(5) *Petaloids in center.*—Few.

(6) *Persistence.*—Drop off cleanly.

(7) *Fragrance.*—Good old rose fragrance.

(8) *Lasting quality.*—Good lasting on plant.

2. REPRODUCTIVE ORGANS

A. Stamens, filaments and anthers:

(1) *Arrangement.*—Regularly arranged around styles.

(2) *Color.*—35C.

B. Pollen:

*Color.*—31C.

C. Styles: Uneven, thin.

D. Stigmas:

*Color.*—31B.

E. Hips:

*Shape.*—Globular.

*Size.*—Small.

*Color.*—26A.

*Do seeds protrude?*—No.

3. PLANT

A. Form: Spreading.

B. Growth: Vigorous, free branching.

*Height attained.*—About 3 to 3½ feet.

C. Foliage: Compound 5 to 7 leaflets.

(1) *Size.*—Medium.

(2) *Quantity.*—Abundant.

(3) *Color.*—New foliage: upper side — near to 137A; under side — near to 147B. Old foliage: upper side — between 137A and 146A; under side — near 147B.

(4) *Shape.*—Ovoid.

(5) *Texture.*—Upper side is waxy and under side is dull.

(6) *Edge.*—Serrated.

(7) *Serration.*—Simple.

(8) *Leaf stem.*—Color — near to 147A. Under side — 147C.

(9) *Stipules.*—Medium.

(10) *Resistance to disease.*—Blackspot — excellent. Mildew — excellent.

D. Wood:

(1) *New Wood.*—Color — near 137D. Bark — smooth.

(2) *Old wood.*—Color — near 137B with wine red cast where exposed to light. Bark — smooth.

E. Thorns:

(1) *Thorns.*—Quantity (main stalk) — ordinary. On laterals from stalk — normal. Form — flat. Length — small. Color — wine red. Position — scattered.

(2) *Prickles.*—Few.

F. Winter hardiness: Very winter hardy.

I claim:

1. A new and distinct variety of rose plant of the floribunda class, substantially as shown and described, characterized particularly by a floriferous, vigorous, free branching spreading plant with abundant foliage and superior disease resistance producing many flowers of overall lavender tonality borne singly and in large sprays.

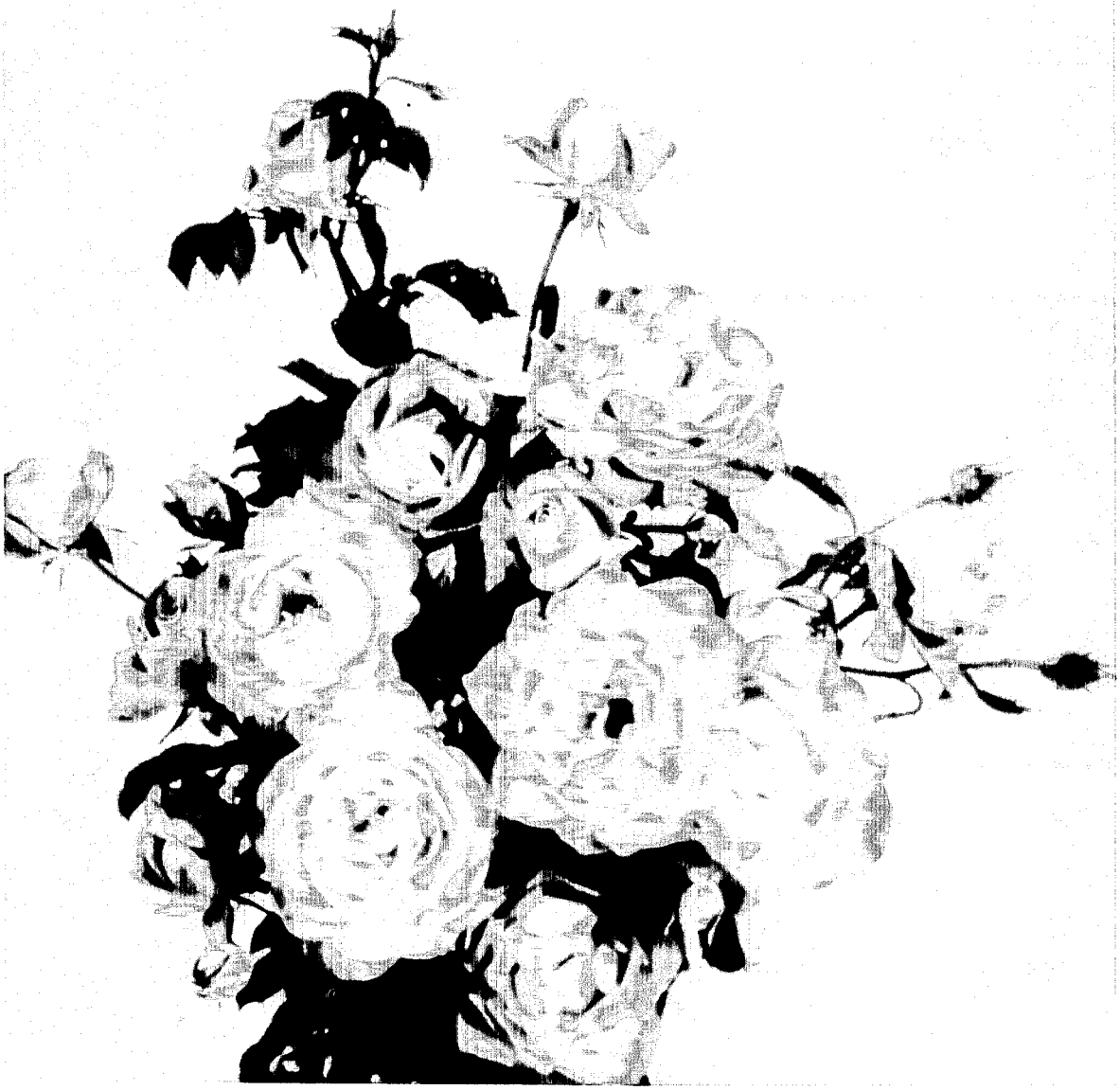

* * * * *